(12) United States Patent
Kimura

(10) Patent No.: US 8,344,730 B2
(45) Date of Patent: Jan. 1, 2013

(54) MAGNETIC RESONANCE IMAGING APPARATUS

(75) Inventor: Tokunori Kimura, Yaita (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 475 days.

(21) Appl. No.: 12/753,461

(22) Filed: Apr. 2, 2010

(65) Prior Publication Data
US 2010/0253342 A1    Oct. 7, 2010

(30) Foreign Application Priority Data
Apr. 3, 2009    (JP) .................................. 2009-091303

(51) Int. Cl.
*G01V 3/00*    (2006.01)
(52) U.S. Cl. ...................................... 324/318; 324/322
(58) Field of Classification Search .......... 324/300–322; 600/407–445
See application file for complete search history.

(56) References Cited

U.S. PATENT DOCUMENTS

| 4,663,772 | A | 5/1987 | Mattson et al. |
| 6,559,644 | B2 | 5/2003 | Froundlich et al. |
| 6,804,546 | B1* | 10/2004 | Thompson et al. ........... 600/410 |
| 6,980,001 | B2* | 12/2005 | Paley et al. ................... 324/318 |
| 8,248,069 | B2* | 8/2012 | Buracas ........................ 324/307 |
| 2008/0071167 | A1 | 3/2008 | Ikedo et al. |
| 2011/0014129 | A1* | 1/2011 | Zabow et al. ................ 424/9.34 |

OTHER PUBLICATIONS

Le Bihan et al., "Direct and fast detection of neuronal activation in the human brain with diffusion MRI", PNAS, vol. 103, No. 21, (May 23, 2006), pp. 8263-8268.

* cited by examiner

*Primary Examiner* — Brij Shrivastav
(74) *Attorney, Agent, or Firm* — Nixon & Vanderhye PC

(57) ABSTRACT

An apparatus includes a unit which acquires, by a first sequence, an MR signal before administration of a contrast agent and which also acquires, by a second sequence, an MR signal after the administration, the first sequence dephasing a magnetization after RE excitation to make a greater signal reduction in a first signal component regarding a fluid flowing within a first range than in a second signal component regarding the fluid flowing within a second less than the first range, the second sequence bringing the MR signal after the administration to a level corresponding to the concentration of the agent, a unit which reconstructs first and second images, and a unit which generates a third image on the basis of the first and second images, the third image showing the degree of a change of the fluid after the administration from a state before the administration.

17 Claims, 14 Drawing Sheets

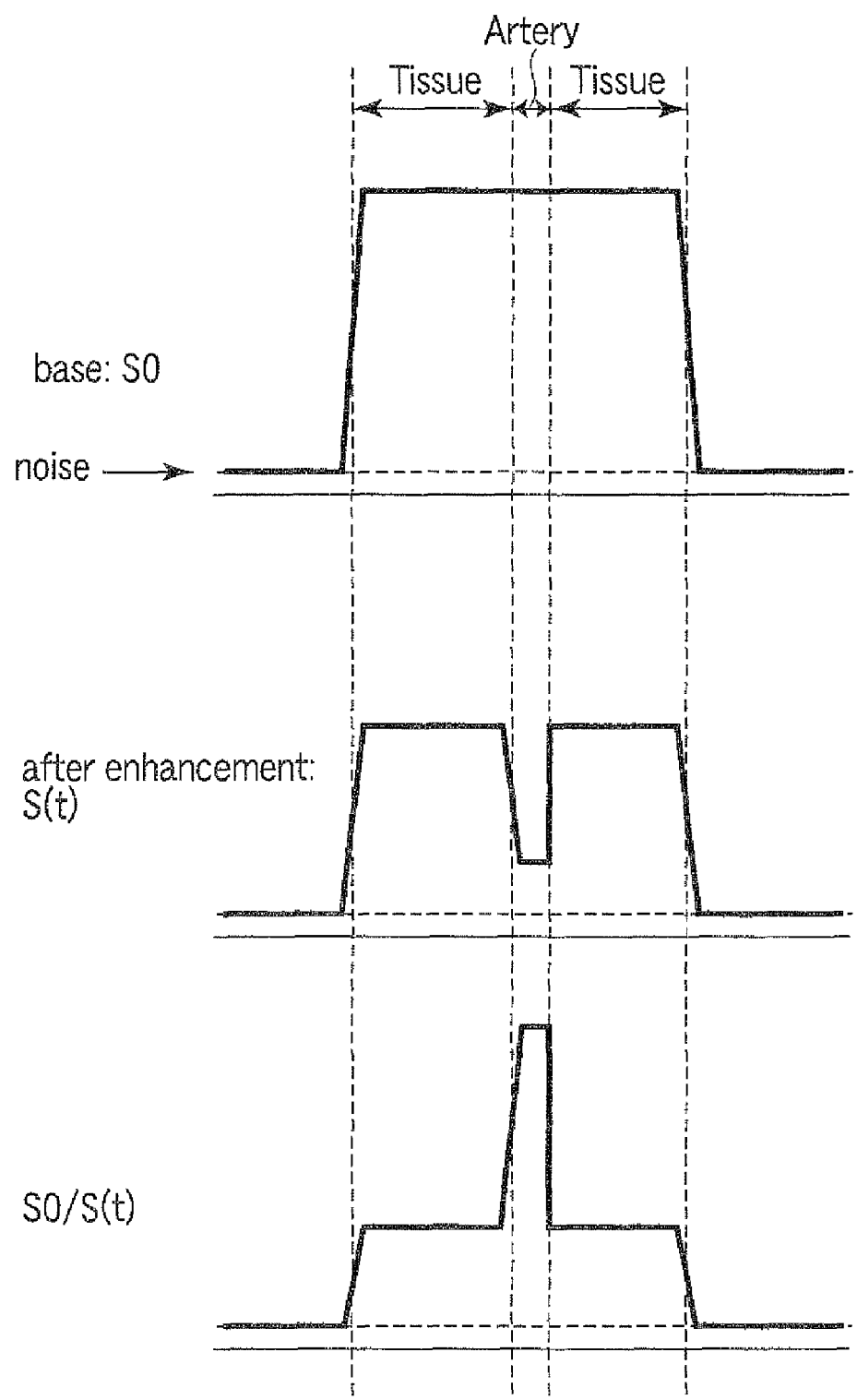
F I G. 10

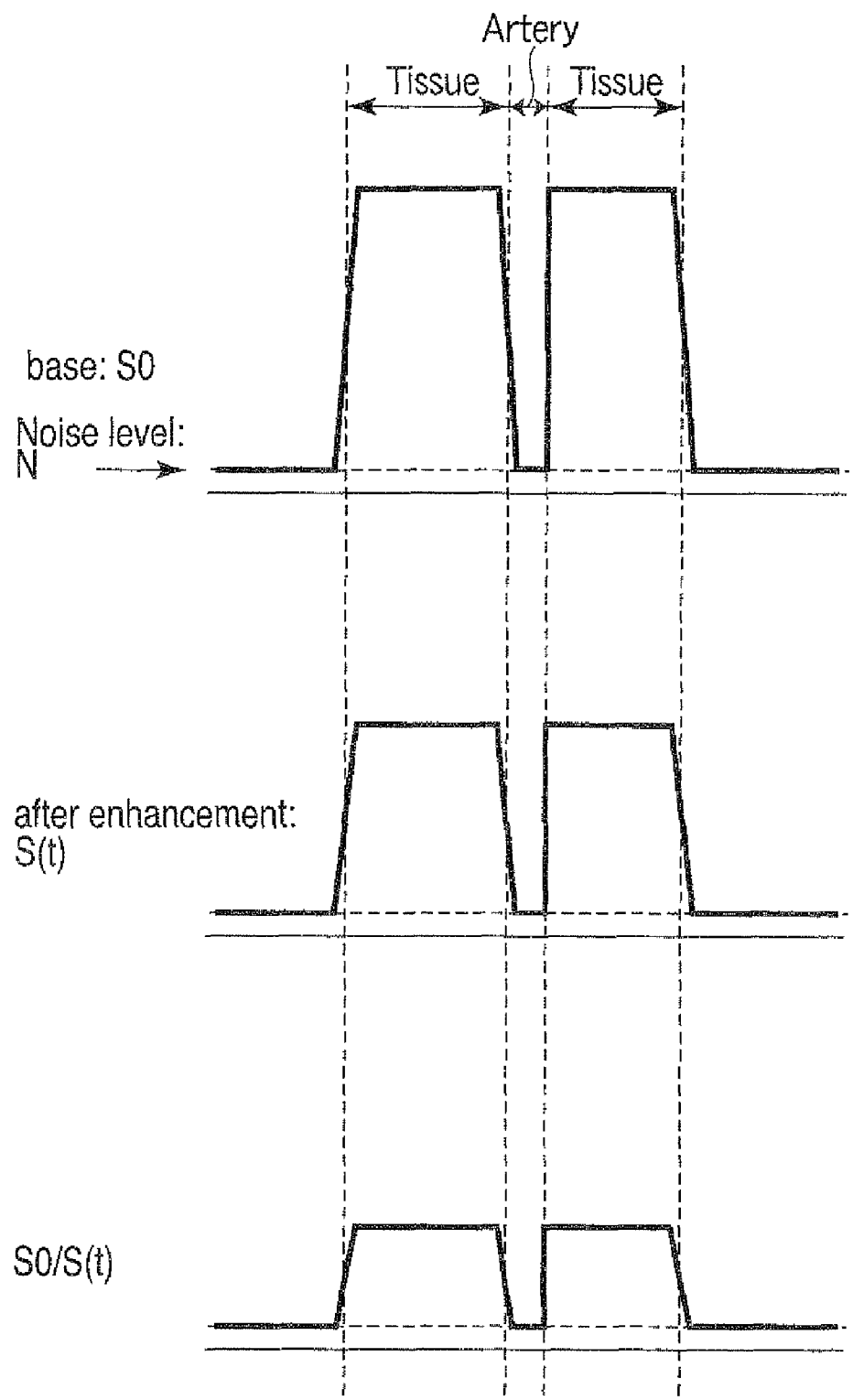
F I G. 12

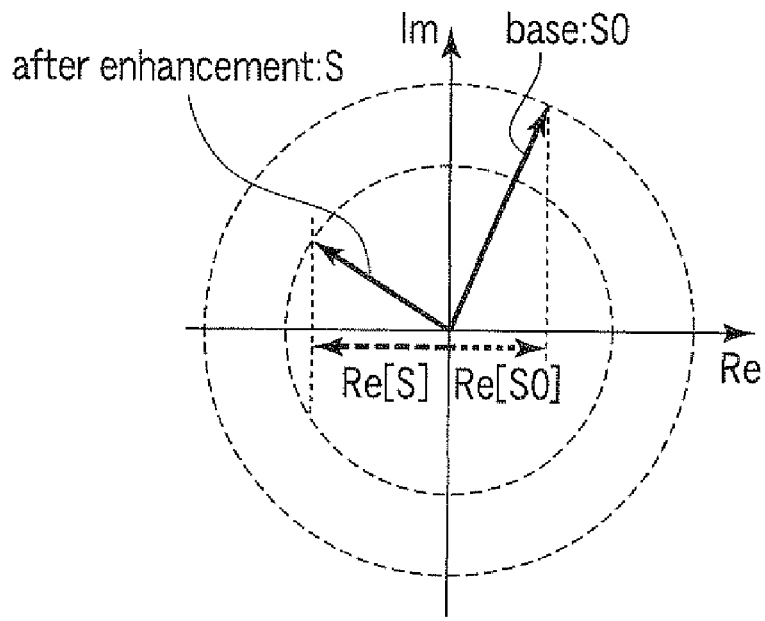
F I G. 20
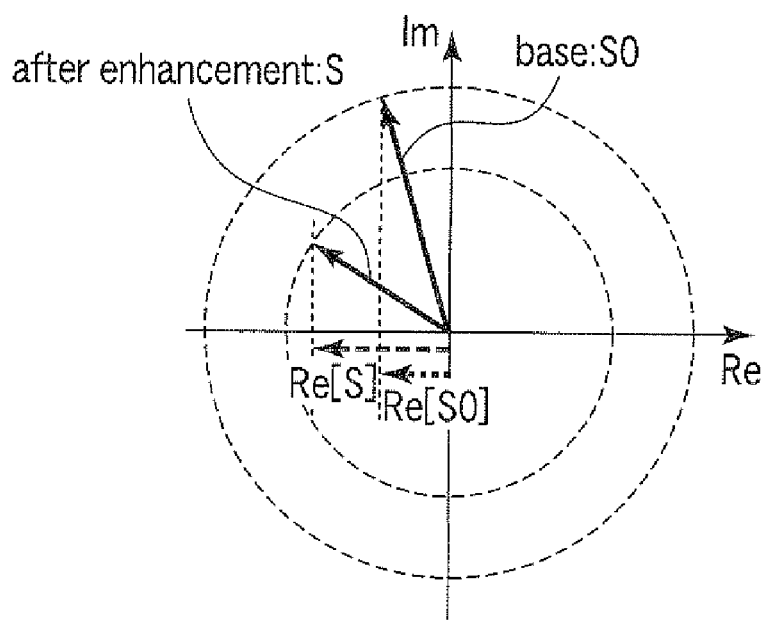
F I G. 21

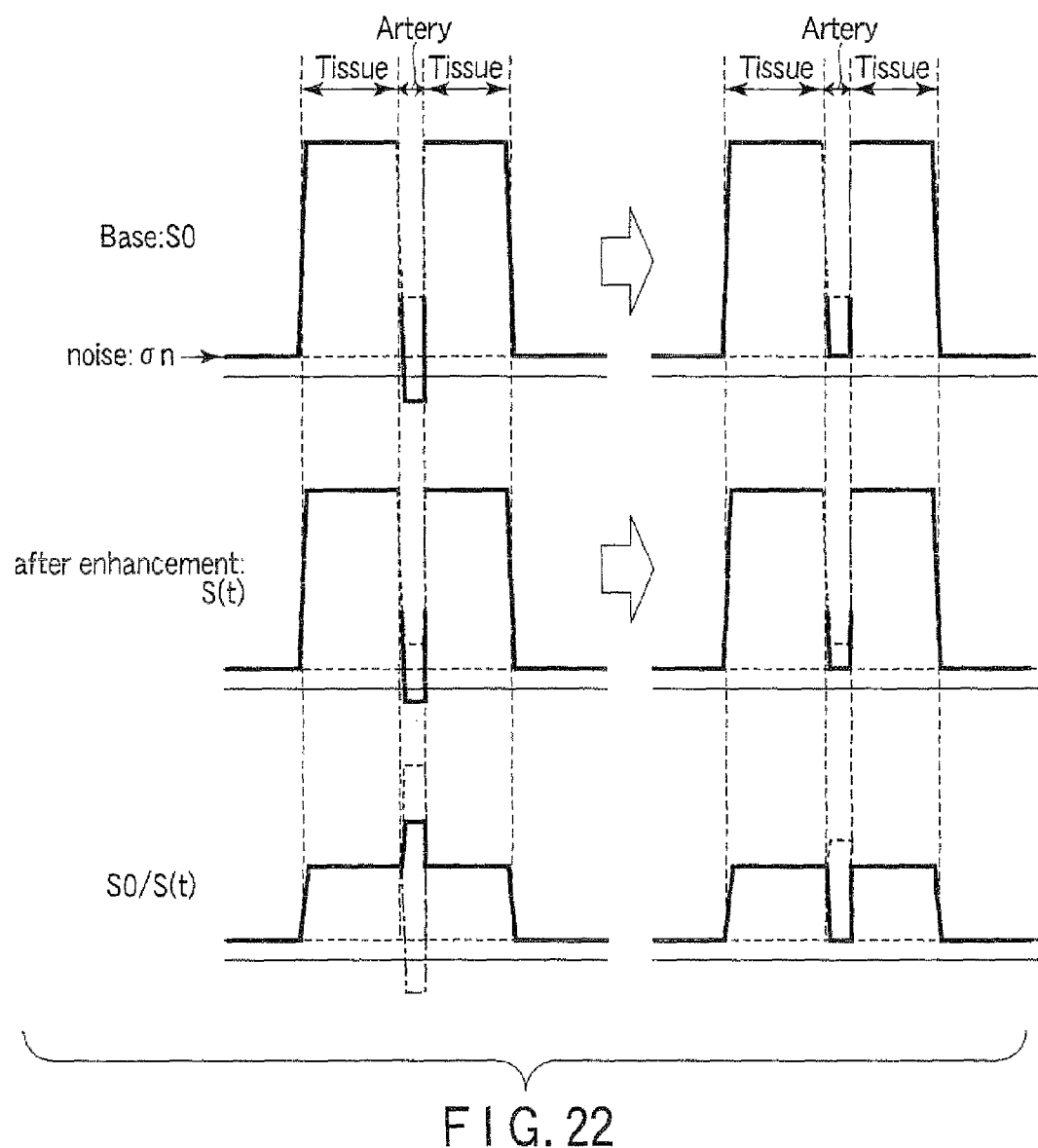
F I G. 22

MAGNETIC RESONANCE IMAGING APPARATUS

CROSS-REFERENCE TO RELATED APPLICATIONS

This application is based upon and claims the benefit of priority from prior Japanese Patent Application No. 2009-091303, filed Apr. 3, 2009, the entire contents of which are incorporated herein by reference.

BACKGROUND OF THE INVENTION

1. Field of the Invention

The present invention relates to an art of obtaining information for a medical diagnosis on the basis of a magnetic resonance signal emitted from a subject.

2. Description of the Related Art

In perfusion imaging which uses an intravascular contrast agent, such as dynamic susceptibility contrast-magnetic resonance imaging (DSC-MRI) or dynamic contrast-enhanced MRI (DCE-MRI), blood vessels disturb a diagnosis and are therefore desirably excluded on a analytical map. Blood vessels can be excluded by image processing such as threshold processing from an image in which the blood vessels are already visualized. This, however, not only requires extra processing but also makes it difficult to set an optimum threshold. Moreover, an image of this kind is generally obtained with low spatial resolution to attach importance to a signal-noise ratio and time resolution. Thus, parenchymal portions located in the vicinity of the blood vessels are also excluded by a partial volume effect. In a method such as a deconvolution method which uses an arterial input function (AIF), blood vessel portions are used for an analysis and therefore cannot be excluded. A spin echo (SE) based method is said to have a higher blood vessel suppression effect than a gradient echo (GRE) based method, but the effect is insufficient.

In functional MRI (fMRI) which uses GRE based echo planar imaging (EPI), changes in the activity of tissue (tissue including capillary vessels) are observed. However, an in-flow effect and a blood oxygenation level dependent (BOLD) effect in a relatively thick blood vessel hinder to the observation of changes in the activity of tissue adjacent to blood vessels in particular. In general spin-warp type GRE which does not use the EPI method, the in-flow effect, in particular, is an artifact for the original BOLD. The image processing has the same problem. In addition, recently reported diffusion-weighted (DW)—fMRI (see "Le Bihan at al. PNAS 103, 8263-8268, 2006") uses a b-factor of 1000 or more, and is mainly directed to separate the variation of a D-coefficient in tissue cells in accordance with the difference of D-coefficient in a tissue interstitial fluid and an intracellular fluid.

Thus, the existing problem is that if fluids flowing at a lower velocity, such as the blood and contrast agent flowing in capillary vessels are visualized, fluids flowing at a higher velocity, such as the blood and contrast agent flowing in arteries and veins, are also visualized.

BRIEF SUMMARY OF THE INVENTION

Under such circumstances, there has been a desire that fluids flowing at a lower velocity can be visualized in a more enhanced manner than fluids flowing at a higher velocity.

According to a first aspect of the present invention, there is provided a magnetic resonance imaging apparatus comprising: an acquisition unit which acquires, by a first sequence, a magnetic resonance signal generated in an imaging region before administration of a contrast agent and which also acquires, by a second sequence, a magnetic resonance signal generated in the imaging region after the administration of the contrast agent, the first sequence dephasing a magnetization after radio frequency excitation to make a greater signal reduction in a first magnetic resonance signal component regarding a fluid flowing within a first flow velocity range than in a second magnetic resonance signal component regarding the fluid flowing within a second flow velocity range less than the first flow velocity range, the second sequence bringing the magnetic resonance signal generated in the imaging region after the administration of the contrast agent to a level corresponding to the concentration of the contrast agent; a reconstruction unit which reconstructs a first image and a second image on the basis of the magnetic resonance signals respectively acquired by the first and second sequences, the first image and the second image showing spatial distributions of the fluid in the imaging region to reflect the intensities of the magnetic resonance signals; and a generation unit which generates a third image on the basis of the first image and the second image, the third image showing the degree of a change of the fluid after the administration of the contrast agent from a state before the administration of the contrast agent.

According to a second aspect of the present invention, there is provided a magnetic resonance imaging apparatus comprising: an acquisition unit which acquires, by a dephase sequence, a magnetic resonance signal generated in an imaging region, the dephase sequence dephasing a magnetization after radio frequency excitation to make a greater signal reduction in a fluid flowing within a first flow velocity range than in the fluid flowing within a second flow velocity range less than the first flow velocity range; and a reconstruction unit which reconstructs an image on the basis of the magnetic resonance signal acquired by the acquisition unit, the image showing a spatial distribution of the fluid in the imaging region to reflect the intensity of the magnetic resonance signal.

According to a third aspect of the present invention, there is provided a magnetic resonance imaging apparatus comprising: an acquisition unit which performs imaging of a subject before administration of a negative contrast agent by a black blood method and performs dynamic imaging of the subject after the administration of the negative contrast agent by a predetermined imaging method, the black blood method reducing a blood vessel signal including a gradient magnetic field dephase pulse to visualize blood vessels in black; a reconstruction unit which reconstructs a base image on the basis of a magnetic resonance signal obtained by the imaging of the subject before the administration of the negative contrast agent and also reconstructs a contrast image of multiple time phases on the basis of a magnetic resonance signal obtained by the dynamic imaging of the subject after the administration of the negative contrast agent; and a generation unit which generates a diagnostic image on the basis of the base image and the contrast image.

According to a fourth aspect of the present invention, there is provided a magnetic resonance imaging apparatus comprising: an acquisition unit which acquires a magnetic resonance signal generated in an imaging region under a first condition and a second condition, the first condition causing the signal level of a first magnetic resonance signal component regarding a fluid flowing within a first flow velocity range to be different in a prescribed direction from the signal level of a second magnetic resonance signal component regarding the fluid flowing within a second flow velocity range less than the first flow velocity range, the second condition causing the signal level of the first magnetic resonance signal component to be different in the prescribed direction from the signal level of the second magnetic resonance signal component, the signal levels of the first and second magnetic resonance signal components being different in the prescribed direction from the signal levels thereof in the first condition, the amount of change of the first magnetic resonance signal component being greater than that of the second magnetic resonance signal component in the second condition; a reconstruction unit which reconstructs a first image and a second image on the basis of the magnetic resonance signals respectively acquired under the first and second conditions, the first image and the second image showing spatial distributions of the fluid in the imaging region to reflect the intensities of the magnetic resonance signals; and a generation unit which generates a third image on the basis of the first image and the second image, the third image showing the degrees of signal level changes in the first condition and the second condition.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10 is a graph showing how the signal value of a diagnostic image is calculated in general dynamic imaging;

FIG. 12 is a graph showing a second example of how the signal value of a diagnostic image is calculated in the dynamic imaging according to one embodiment;

FIG. 20 is a graph showing one example of a blood vessel signal after the background phase correction and the cosine filter processing and before and after enhancement;

FIG. 21 is a graph showing one example of a blood vessel signal after the background phase correction and the cosine filter processing and before and after enhancement; and FIG. 22 is a graph showing the effect of the cosine filter processing in the form of blood vessel and background spatial profiles.

DETAILED DESCRIPTION OF THE INVENTION

Embodiments of the present invention will be hereinafter described with reference to the drawings.

Figure 1:
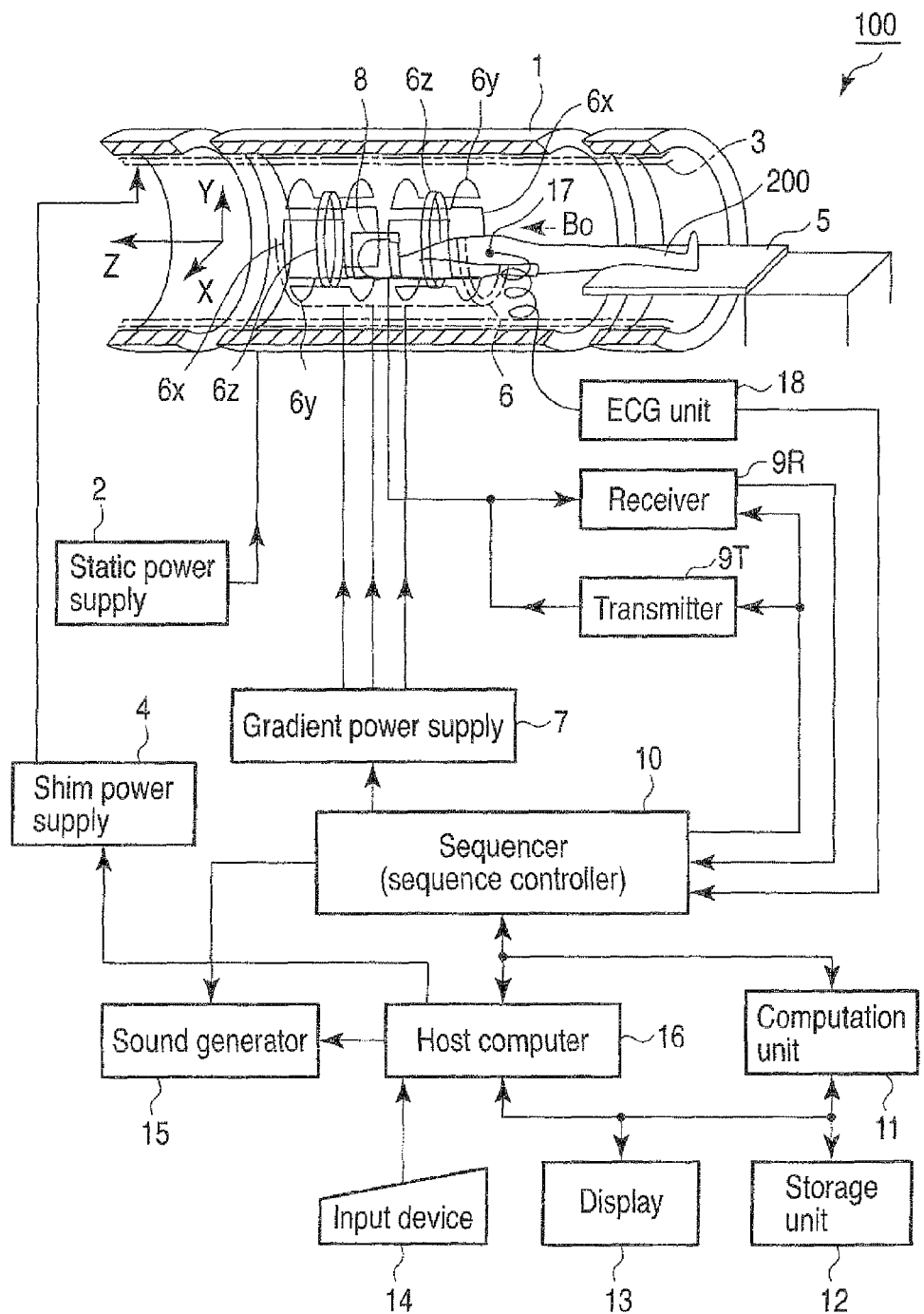
FIG. 1 is a diagram schematically showing the configuration of a magnetic resonance imaging apparatus (MRI apparatus) according to one embodiment.

FIG. 1 is a diagram showing the schematic configuration of a magnetic resonance imaging apparatus (MRI apparatus) 100 according to the present embodiments.

The MRI apparatus 100 comprises a bed unit, a static-magnetic-field generating unit, a gradient-magnetic-field generating unit, a receiving/transmitting unit, and a control/operating unit. The bed unit moves a subject 200 mounted thereon. The static-magnetic-field generating unit generates a static magnetic field. The gradient-magnetic-field generating unit generates a gradient magnetic field designed to add position information to the static magnetic field. The receiving/transmitting unit receives and transmits a radio-frequency signal. The control/operating unit controls the whole system and reconstructs images. The MRI apparatus 100 has, as components of these units, a magnet 1, a static magnetic power supply 2, a shim coil 3, a shim power supply 4, a top plate 5, a gradient coil unit 6, a gradient power supply 7, an RF coil unit 8, a transmitter 9T, a receiver 9R, a sequencer (sequence controller) 10, an computation unit 11, a storage unit 12, a display 13, an input device 14, a sound generator 15, and a host computer 16. Connected to the MRI apparatus 100 is an electrocardiograph unit which measures an EGG signal as a signal representing the cardiac pulsation of the subject 200.

The static-magnetic-field generating unit includes the magnet 1, the static magnetic power supply 2, the shim coil 3 and the shim power supply 4. For example, a superconducting magnet or a normal conducting magnet can be used as the magnet 1. The static magnetic power supply 2 supplies a current to the magnet 1. In addition, the static magnetic power supply 2 can be omitted when the superconducting magnet is employed as the magnet 1. The static-magnetic-field generating unit therefore generates a static magnetic field $B_0$ in a cylindrical space (diagnostic space) into which the subject 200 is moved. The direction of the static magnetic field $B_0$ virtually coincides with the axial direction (Z-axis direction) of the diagnostic space. The shim coil 3 generates a correction magnetic field for rendering the static magnetic field uniform when a current is supplied to it from the shim power supply 4 under the control of the host computer 16.

The bed unit moves the top plate 5, on which the subject 200 is lying, into or out of the diagnostic space.

The gradient-magnetic-field generating unit includes the gradient coil unit 6 and the gradient power supply 7. The gradient coil unit 6 is arranged in the magnet 1. The gradient coil unit 6 has three coils 6x, 6y and 6z that generate gradient magnetic fields extending in mutually orthogonal X-, Y- and Z-axes, respectively. The gradient power supply 7 supplies pulse currents for generating gradient magnetic fields to the coils 6x, 6y and 6z, under the control of the sequencer 10. The gradient-magnetic-field generating unit controls the pulse currents supplied from the gradient power supply 7 to the coils 6x, 6y and 6z. Thus, the gradient-magnetic-field generating unit synthesizes gradient magnetic fields extending in the three physical axes (the X-, Y- and Z-axes), respectively. The unit sets these magnetic fields in logical axes defined by a slice direction gradient magnetic field Gs, a phase-encode direction gradient magnetic field Ge and a read-out direction (frequency-encode) gradient magnetic field Gro, respectively, which intersect at right angles with one another. The slice, phase-encode and read-out direction gradient magnetic fields, Gs, Ge and Or are superposed on the static magnetic field $B_0$.

The receiving/transmitting unit includes the RF coil unit 8, the transmitter 9T, and the receiver 9R. The RF coil unit 8 is arranged in the vicinity of the subject 200 in the diagnostic space. The transmitter 9T and the receiver OR are connected to the RE coil unit 8. The transmitter 9T and the receiver 9R operate under the control of the sequencer 10. The transmitter 9T supplies an RF current pulse of Lamor frequency to the RF coil unit 8 in order to induce nuclear magnetic resonance (NMR). The receiver 9R acquires an MR signal (radio-frequency signal), such as an eco signal, which the RF coil unit 8 has received. The receiver 9R then performs, on the MR signal, various processes, such as pre-amplification, intermediate-frequency conversion, phase detecting, low-frequency amplification and filtering. Finally, the receiver 9R performs analog-to-digital (A/D) conversion on the MR signal, producing digital data (raw data).

The control/operating unit includes the sequencer 10, the computation unit 11, the storage unit 12, the display 13, the input device 14, the sound generator 15 and the host computer 16.

The sequencer 10 has a CPU and a memory. The sequencer 10 stores, into the memory, pulse sequence information transmitted from the host computer 16. The CPU of the sequencer 10 controls the operations of the gradient power supply 7, transmitter 9T and receiver 9R in accordance with the sequence information stored in the memory. The CPU of the sequencer 10 also receives the raw data output from the receiver 9R and transfers the raw data to the computation unit 11. Note that the sequence information is all data necessary for operating the gradient power supply 7, transmitter 9T and receiver 9R in accordance with the pulse sequence. It includes, for example, information about the intensity of the pulse current supplied to the coils 6x, 6y and 6z, the period of applying the pulse current and the timing of applying the pulse current.

The computation unit 11 receives the raw data output from the transmitter 9T, through the sequencer 10. The computation unit 11 has an internal memory. The internal memory has a k-space (also called Fourier space or frequency space), in which the raw data input to the computation unit 11 is placed. The computation unit 11 subjects the data placed in the k-space to two- or three-dimensional Fourier transform, thereby reconstructing video data for the real space. The computation unit 11 can perform, if necessary, synthesis and differential operations (including weighted differentiation) on any data representing an image. The synthesis includes cumulative addition of pixel values, maximum intensity projection (MIP), minimum intensity projection (minIP), and the like. As another example of the synthesis, the axes of several frames may be aligned in a Fourier space, and the raw data items representing these frames may be synthesized, thereby generating one-frame raw data. The addition of pixel values includes, for example, simple addition, addition averaging or weighting addition.

The storage unit 12 stores video data reconstructed or video data subjected to the above-mentioned synthesis or differential processing.

The display 13 displays various images to be presented to a user, under the control of the host computer 16. For example, a display device such as a liquid crystal display can be used as the display 13.

The input device 14 is operated to input various types of information, such as parameter information for selecting synchronization timing desired by the operator, scanning conditions, the pulse sequence, information about the image synthesis and differential operation, and the like. The input device 14 sends the input information to the host computer 16. The input device 14 comprises, as the case may be, a pointing device such as a mouse or a track ball, a selection device such as a mode change switch, or an input device such as keyboard.

The sound generator 15 generates messages for the start and end of breath holding as sounds when instructed by the host computer 16.

The host computer 16 controls the operation of every unit of the MRI apparatus 100 to achieve various operations achieved by existing MRI apparatuses.

The electrocardiograph unit includes an ECG sensor 17 and an ECG unit 18. The ECG sensor 17 is attached to the surface of the body of the subject 200, and detects an ECG signal of the subject 200 as an electric signal (hereinafter referred to as a sensor signal). The ECG unit 18 subjects the sensor signal to various kinds of processing, including digitization, and then outputs it to the host computer 16 and the sequencer 10. For example, a vector electrocardiograph can be used as the electrocardiograph unit. The sequencer 10 uses the sensor signal generated by the electrocardiograph unit, when it is necessary to carry out a scan in synchronization with the cardiac phase of the subject 200.

Now, the operation of the MRI apparatus 100 having the above-described configuration is described. It is to be noted that the MRI apparatus 100 is capable of performing various kinds of imaging that have been enabled by existing MRI apparatuses, which is, however, not described. Moreover, in the operation described here, tissue including capillary vessels (hereinafter simply refer to as tissue) is visualized by DSC-MRA so that blood vessels such as arteries and veins in which blood flows at a relatively high velocity (hereinafter simply refer to as blood vessels) are excluded.

(Basic Operation)

The MRI apparatus 100 performs imaging by a pulse sequence in which lateral magnetization or longitudinal magnetization after RE excitation is dephased by a proper b-factor so that signals are more reduced in parts having more motion by a motion probing gradient (MPG).

Figure 2:
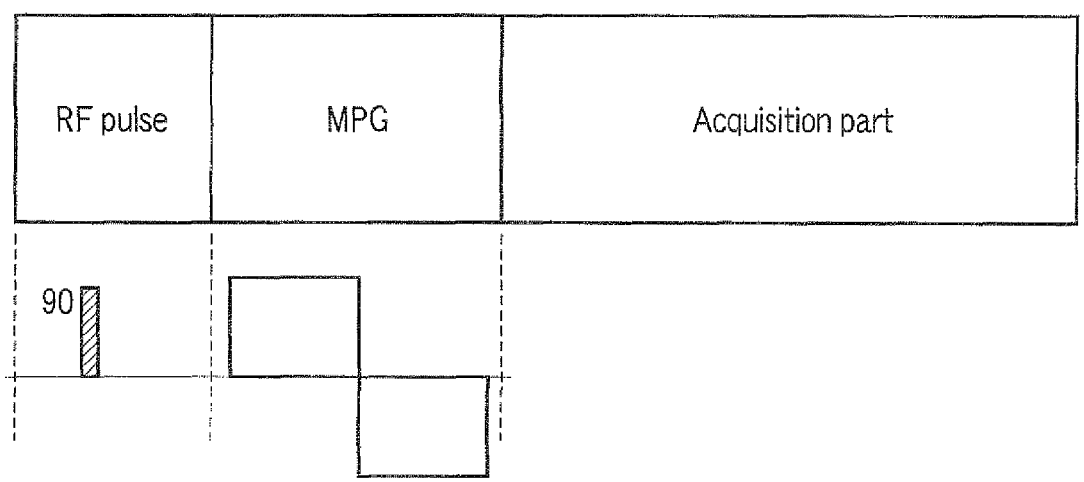
FIG. 2 is a diagram showing one example of a pulse sequence to dephase lateral magnetization.
Figure 3:
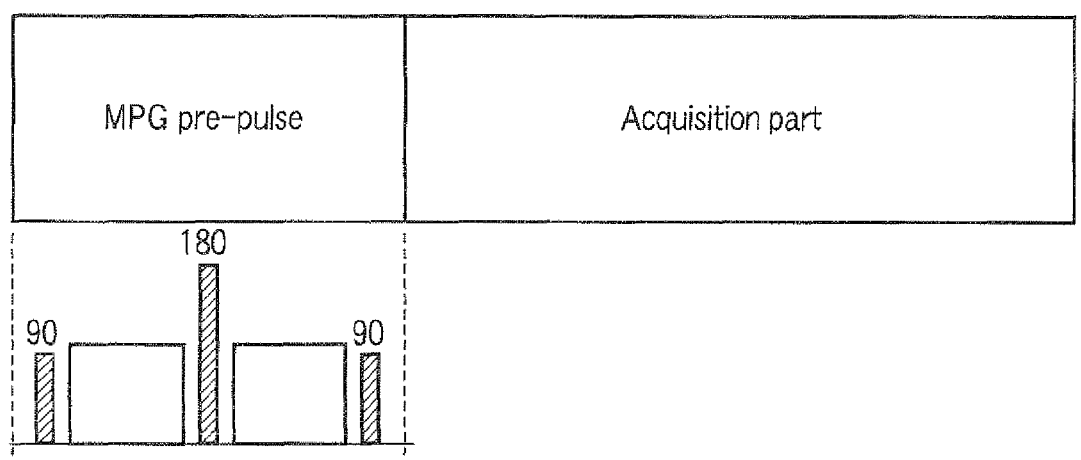
FIG. 3 is a diagram showing one example of a pulse sequence to dephase longitudinal magnetization.

FIG. 2 is a diagram showing one example of a pulse sequence to dephase the lateral magnetization. FIG. 3 is a diagram showing one example of a pulse sequence to dephase the longitudinal magnetization.

In the pulse sequence shown in FIG. 2, an RF pulse is applied, and then the MPG is applied before the start of an acquisition part for acquiring a magnetic resonance signal. In this case, a GRE or EPI, for example, is suitable for the pulse sequence in the acquisition part.

In the pulse sequence shown in FIG. 3, an MPG pre-pulse is applied before the start of an acquisition part. The MPG pre-pulse is in the form of, for example, 90° pulse-MPG-180° pulse-MPG-90° pulse. As a pulse sequence in the acquisition part in this case, a fast field echo (FFE), steady state free precession (SSFP) or fast spin echo (FSE), for example, is used. In addition, the pulse sequence shown in FIG. 3 is called a preparation scheme.

The present embodiment is characterized in that a subject to which a negative contrast agent is administered is dynamically imaged by a black blood method that uses a pulse sequence including a gradient magnetic field dephase pulse. The black blood method is an imaging method which reduces blood vessel signals to visualize blood vessels in black. A generally used gradient magnetic field dephase pulse may be used, but in the present embodiment, the MPG pulse shown in FIG. 2 and FIG. 3 is used as the gradient magnetic field dephase pulse.

The amount of dephasing by the MPG pulse is set at such a b-factor that has no influence on parenchymal portions and its contrast components other than blood vessels. The b-factor is associated with the velocity and spatial distribution (a direction in a voxel and the degree of a direction change) of a fluid such as blood (contrast agent). In particular, the b-factor ranges, for example, from 2 to 10 [sec/mm$^2$]. More particularly, the b-factor ranges from 2 to 4 [sec/mm$^2$].

In the present embodiment, the black blood method including the gradient magnetic field dephase pulse is applied to an imaging sequence for obtaining images before and after the administration of the contrast agent. However, the black blood method including the gradient magnetic field dephase pulse may be applied to an imaging sequence for obtaining a base image before the administration of the contrast agent, and an imaging sequence which includes no gradient magnetic field dephase pulse (no gradient magnetic field rephase pulse is applied or no gradient magnetic field rephase and dephase pulses are applied) may be used to obtain an image after the administration of the contrast agent.

Figure 4:
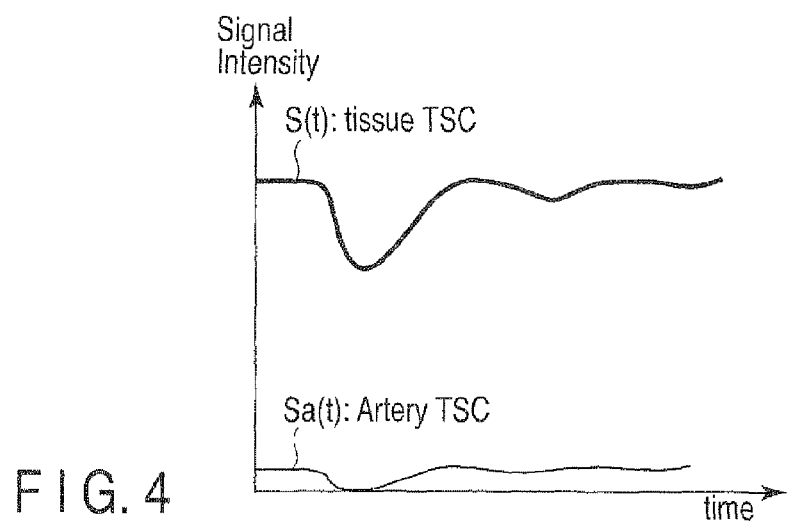
FIG. 4 is a graph showing an original signal intensity-time curve in the case where a negative contrast agent is used.

On the other hand, a contrast agent is generally used to visualize tissue including capillary vessels. An original signal intensity-time curve (time-signal curve: TSC) in the case where contrast imaging is performed in accordance with the above-mentioned pulse sequence using the above-mentioned b-factor is as shown in FIG. 4. The tissue TSC is a TSC concerning tissue, and an artery TSC is a TSC concerning arteries. It should, however, be noted that FIG. 4 is a graph showing an original signal intensity-time curve in the case where a negative contrast agent is used.

Contrast agent concentration C(t) for the tissue TSC and contrast agent concentration Ca(t) for the artery TSC are obtained by the following equations, respectively:

$$C(t) = \ln [S0/S(t)]/TE$$

$$Ca(t) = \ln [S0/Sa(t)]/TE$$

wherein S(t) is the original signal intensity for the tissue TSC, Sa(t) is the original signal intensity for the artery TSC, S0 and S(t) are images before and after the administration of the contrast agent, and TE is an echo time.

Figure 5:
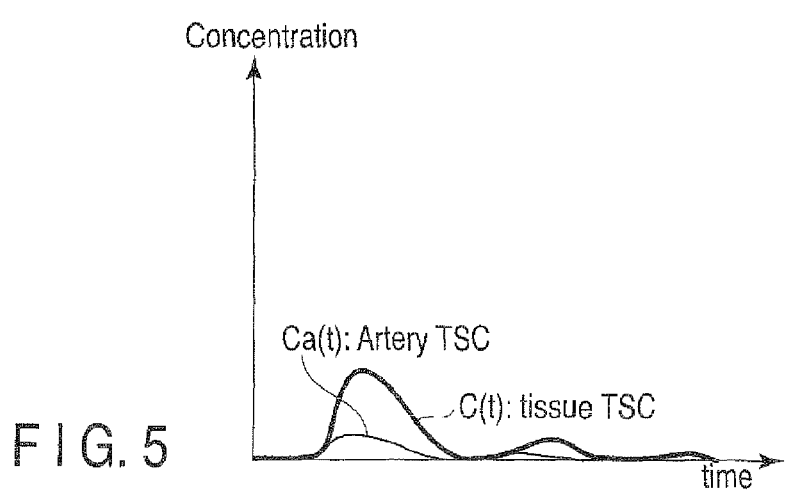
FIG. 5 is a graph showing a concentration-time curve obtained from the original signal intensity-time curve shown in FIG. 4.

Thus, a concentration-time curve as shown in FIG. 5 is obtained from the original signal intensity-time curve shown in FIG. 4.

Figure 6:
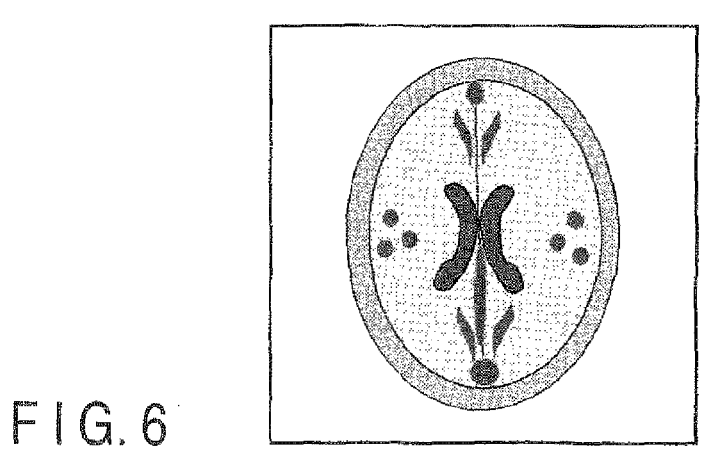
FIG. 6 is a diagram showing one example of a CBF map.

As apparent from FIG. 5, the peak of the concentration of the artery TSC is lower than the peak of the concentration of the tissue TSC. As a result, artery regions in a cerebral blood flow (CBF) map are suppressed. FIG. 6 is a diagram showing one example of a CBF map obtained according to the present embodiment.

Figure 7:
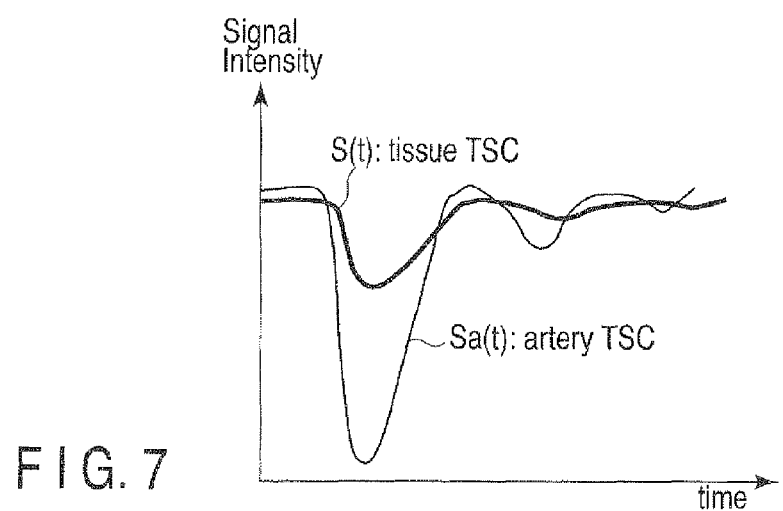
FIG. 7 is a graph showing an original signal intensity-time curve in the case of a general DSC-MRA.
Figure 8:
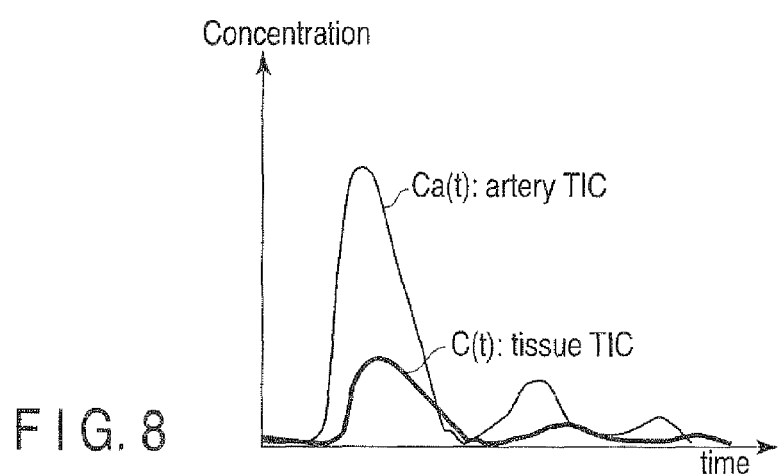
FIG. 8 is a graph showing a concentration-time curve obtained from the original signal intensity-time curve shown in FIG. 7.
Figure 9:
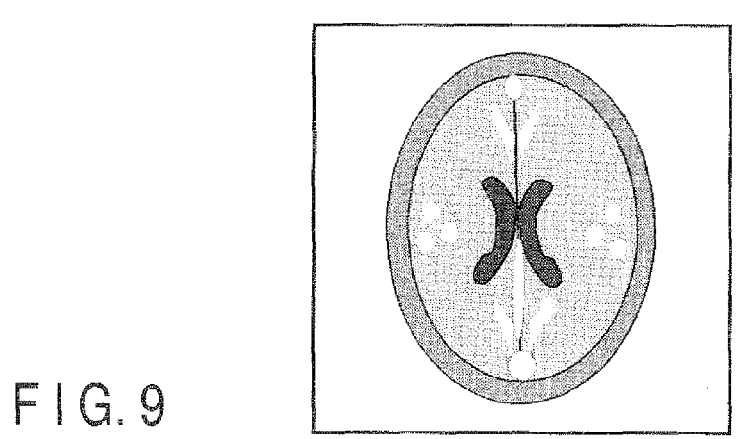
FIG. 9 is a diagram showing one example of a CBF map in the case of the general DSC-MRA.

On the contrary, in the case of general DSC-MRA, an original signal intensity-time curve, a concentration-time curve and a CBF map are as shown in FIG. 7 to FIG. 9, respectively. That is, the peak of the concentration of the artery TSC is higher than the peak of the concentration of the tissue TSC, and the artery regions in the CBS map are more enhanced than tissue regions.

Thus, in the imaging that does not use the dynamic imaging together, an image in which tissue is visualized in a more enhanced state than arteries can be obtained according to the present embodiment.

(Dynamic Imaging)

In the dynamic imaging, a medical diagnostic image is generated by taking a ratio between an image reconstructed from magnetic resonance signals acquired before enhancement (hereinafter referred to as a base image) and an image reconstructed from magnetic resonance signals acquired after the start of enhancement (hereinafter referred to as a dynamic image). That is, a value obtained by S0/S(t) is used as a signal value for the medical diagnostic image, wherein S0 and S(t) are signal values of the base image and the dynamic image of a given pixel.

However, in general, the dynamic imaging only requires that imaging conditions for obtaining the base image and the dynamic image be different. That is, using the base image and the dynamic image as the images before and after enhancement is one example of the dynamic imaging. It is known that the imaging condition in the dynamic imaging is changed depending on various factors such as an imaging sequence to be applied, a dephasing amount or a load on the subject.

In general, MR signal intensity (amplitude) in the case where a contrast agent is used is represented by Equation (1).

$$S = K \cdot A(T1, \Delta R1^*, TR) \cdot A(T2, TE) \cdot A(\Delta R2^*, TE) \cdot A(D_{flow}, ADC, b) \quad (1)$$

wherein included parameters are defined as follows:

K: a coefficient such as a gain determined by hardware, which is regarded as being the same in one study T1 relaxation term: $A(T1, TR) = 1 - \exp[-TR(1/T1 + \Delta R1^*)]$ $\Delta R1^*$: T1 relaxation velocity attributed to a contrast agent T2 relaxation term: $A(T2, TE) = \exp[-TE/T2]$ T2 relaxation term attributed to a contrast agent: $A(\Delta R2^*, TE) = \exp[-\Delta R2^* TE]$ $\Delta R2^*$: T2 relaxation velocity attributed to a contrast agent Term attributed to flow and diffusion: $A(D_{flow}, ADC, b) = \exp[-b^*(D_{flow} + ADC)]$ Dflow: phase diffusion equivalent component attributed to flow ADC: diffusion coefficient (a) When Negative Enhancement Effect is Used In the DSC-MRI, T1 is constant owing to the administration of the contrast agent, and $\Delta R2^*$ can be regarded as changing with time.

An ideal ratio of signal intensity S after enhancement to signal intensity S0 before enhancement is represented by Equation (2).

$$S/S0 = A(\Delta R2^*, TE) = \exp[-\Delta R2^* TE] \quad (2)$$

As apparent from Equation (2), other terms including the term that contains the b-factor are cancelled.

However, an SNR is neglected in this case, and the situation is different in the presence of noise.

If the SNR is sufficiently reduced to about a noise level in the base image, there is almost no further signal reduction even when a contrast agent is contained. An analysis is typically made with an absolute value image in most cases, and the average value of noise is therefore not equal to or less than a given positive value.

If A(Dflow, ADC, b) is decreased to near 0 by setting b>0 so that the blood vessel signal is reduced to about the noise level in Equation (1), the AIF obtained in Equation (2) has a characteristic shaped with a collapsed head. If the signal intensity S of a blood vessel portion is completely equal to the noise level before and after enhancement, the solution of Equation (2) is 1. That is, enhanced parts are equal to non-enhanced parts. Even when the signal reduction to the noise level is imperfect in this case, the influence of blood vessels is less at the time of an analysis if the magnitude of the AIF is reduced to about the magnitude of a time-intensity curve (TIC) of tissue as a consequence. Smoothing on the absolute value image in terms of space and time lessens the variation of the curve in the time direction resulting from noise.

That is, in the general dynamic imaging with b=0, the blood vessels and tissue are substantially equal in S0 in the base image, but the blood vessels are much lower in S than tissue in the dynamic image, as shown in FIG. 10. Therefore, blood vessels are much lower in S than tissue in a diagnostic image, while blood vessels are enhanced in a contrast agent concentration converted image.

Figure 11:
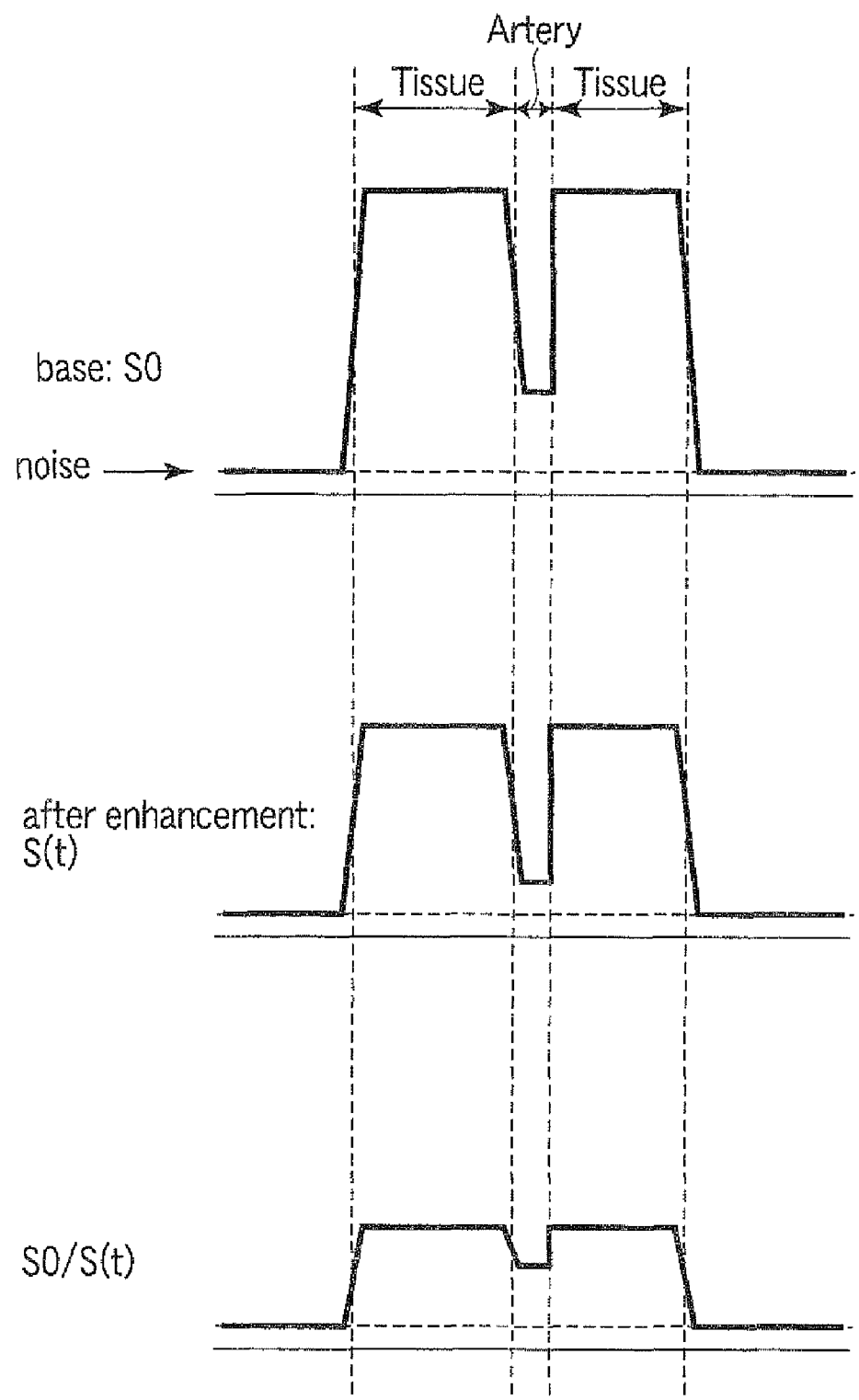
FIG. 11 is a graph showing a first example of how the signal value of a diagnostic image is calculated in dynamic imaging according to one embodiment.

However, in the present embodiment, S0 is closer to the noise level for blood vessels than tissue in the base image, as shown in FIG. 11. Therefore, the decreasing rate of S attributed to the inflow of the contrast agent is lower for blood vessels than tissue. As a result, blood vessels are lower in S than tissue in the diagnostic image, and the influence of blood vessels is reduced.

Furthermore, if the b-factor is set at a proper value at which S0 of blood vessels can be lowered to about the noise level as shown in FIG. 12, S0 of blood vessels in the diagnostic image can be substantially equal to the noise level. As a result, in the diagnostic image, blood vessels can be visualized similarly to the surrounding tissue which includes no capillary vessels, and the influence of blood vessels can be further reduced.

A correct AIF cannot be obtained by b>0, but a perfusion analysis with reduced influence of blood vessels is obtained. Moreover, by reducing to a level substantially equal to that of the surrounding tissue, the influence on tissue around blood vessels is smaller even with smoothing involved than in the perfusion analysis with b=0. Since the blood volume CBV of tissue is as low as 3%, a blood vessel signal in which blood accounts for 100% is 100/3=33 times as high as tissue. Therefore, the influence of the blood vessel signals is easily made in a perfusion measurement method using an angiographic contrast agent, particularly in the DCE-MRI and DSC-MRI, and the effect of reducing the blood vessel signals is important in improving accuracy. Moreover, an imaging condition is more important when a partial volume effect is greater due to an increased slicing thickness resulting from a reduced matrix size.

(b) When Positive Enhancement Effect is Used

The ratio of S after enhancement to S0 before enhancement is represented by Equation (3).

$$S/S0=A(\Delta R2^*,TE)=1-\exp[-TR(1/T1+\Delta R1)] \quad (3)$$

That is, the same goes for the reduction of blood vessel portions in connection with noise as in the case where the negative contrast agent is used.

However, T1 needs to be measured or supposed in order to calculate $\Delta R1^*$, but $\Delta R1^*$ can be calculated, from an image obtained at two or more TR levels before the administration of the contrast agent.

The term A (Dflow, ADC, b) of b contributes to the difference of signal intensity before and after enhancement as a given weight on the whole signal. Thus, if b>0, a blood vessel portion is multiplied by a given value scaled at a lower rate than a tissue portion, so that blood vessel signals are reduced.

$$S-S0=K \cdot A(T2,TE) \cdot A(\Delta R2^*,TE) \cdot A(Dflow,ADC,b) \cdot [\{1-\exp[-TR/T1]\}-\{1-\exp[-TR(1/T1+\Delta R1^*)]\}] \quad (4)$$

The b-factor attributed to an MPG for flow dephase is increased if complete BB is attempted. Therefore, the ATE has only to be substantially as high as tissue TIC.

TE (TE-50 to 80 ms in the case of brain) substantially equal to the T2* or T2 value of tissue is considered to be suitable in the DSC-MRI or DCE-MRI, so that there is a time to allow a small MPG of about b<10 [sec/mm$^2$] that can reduce blood vessel signals to be put between TEs.

(c) Application to fMRI fMRI using BOLD is often used as a brain function examination method, and its effect used is that signal intensity is enhanced as compared with that at rest by the decrease of deoxy-hemoglobin relative to oxy-hemoglobin due to a blood flow increase resulting from nerve stimulation. On the other hand, high signal intensity is also created by the inflow of more blood having saturated longitudinal magnetization into a slab due to an increased blood flow velocity than at rest. However, the in-flow effect is not uniform in the slab and depends on the flow velocity and is thus not necessarily correlated with the increase of blood flow, so that the in-flow effect serves as an artifact. Originally, a BOLD effect alone, in particular, the change of a capillary vessel level should be observed.

The present embodiment uses a GRE based sequence provided with such a b-factor (b=about 2 to 10) that reduces a signal of relatively thick blood vessel to the noise level.

Then, the present embodiment is applicable to even 3D-GRE capable of three-dimensional (3D) acquisition. Regarding time resolution, an acquisition time of about 30 sec for one occasion is enough because the period of stimulation is about one minute. At about b<10, flow in capillary vessels remains, and no high SNR is therefore needed. Thus, if the fMRI is carried out in accordance with the magnetic resonance signals acquired by such a sequence of the present embodiment, the BOLD effect alone can be observed as the change of a capillary vessel level. In addition, the technique disclosed in Nonpatent document 1 is DW-fMRI to observe not blood flow but cellular alterations, so that the b-factor is high, and there are almost zero signals in capillary vessels.

When the sequence according to the present embodiment is applied to the fMRI, a sequence such as GRE-EPI, spin warp GRE, gradient- and spin-echo (GRASS) or asymmetric spin echo (ASE) is also applicable.

(d) Combination of Dephase Intensities Varying by Time Phase

The following holds true with the cases described above. A sequence having the same MPG(b) intensity may be used throughout dynamic time phases. However, when AIF is to be used together, a sequence in which different intensities of MPG(b) are added to time phase blocks may be used. For example, the base image is set at b=2 to 10 at an initial time phase, and in the subsequent time phases, imaging is performed at b=0. That is, the b-factor for obtaining the base image is set to be higher than the b-factor for obtaining the dynamic image. Then, a mask for excluding blood vessels using, for example, a threshold may be created from the base image, and this mask may be used for the subsequent region selection in the time phase image. If the difference between rephase and dephase is used in this case, the position of a blood vessel can be more easily identified. According to the conventional methods, the position of a blood vessel is only recognized after enhancement and after images of all time phases are examined. On the other hand, according to the present embodiment, the position of a blood vessel can be identified before enhancement or before an activation study, so that a dynamic image of a change from the real-time base image with no blood vessel artifact can be displayed or an analytic mapping image can be instantaneously displayed. Moreover, these methods can also be applied to an analytic method using the AIF. Further, when the base image S0 is obtained, adding not only b>0 but also b=0 makes it possible to adapt to both methods.

(e) Application of Rephase

The variation of, for example, pulsation per time phase varies blood vessel signals, which disturbs a correct measurement. In this case, the above-mentioned application of dephase also contributes to the stabilization of blood vessel signals, but the use of rephase, on the contrary, makes it possible to measure a stable AIF with less influence of flow variation per time phase. The exclusion of the blood vessel artifact is difficult in contrast with the above-mentioned advantages (a) to (d) in the case of dephase, but there is a different advantage of stably obtaining AIF.

(f) Method of Stable Blood Vessel Removal by Image Processing

In the (a) described above, blood vessels can be visualized similarly to the surrounding tissue by properly setting the b-factor so that the signal value of blood vessels may be substantially equal to the noise level. However, setting such a proper b-factor is not easy.

Figure 13:
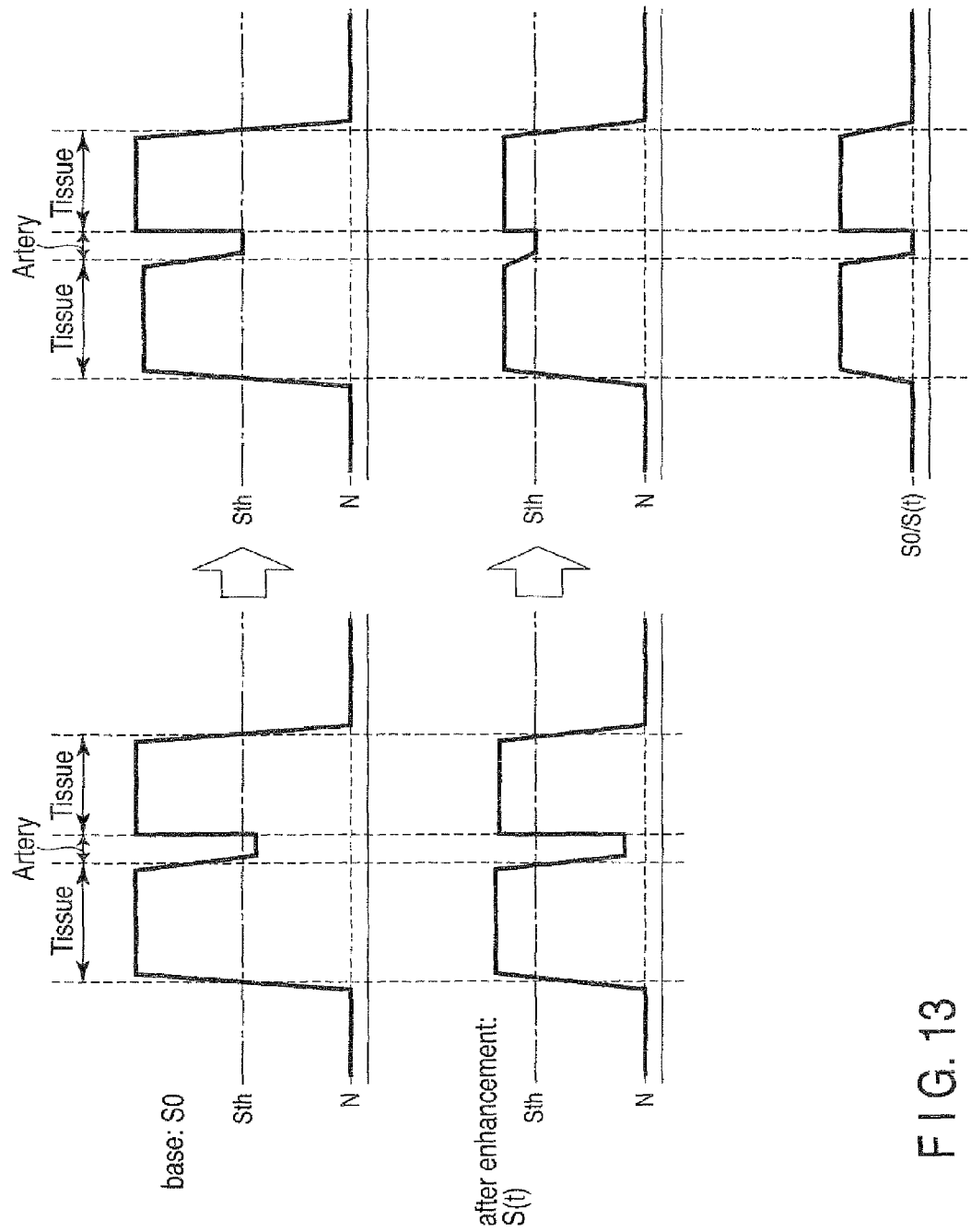
FIG. 13 is a graph showing a third example of how the signal value of a diagnostic image is calculated in the dynamic imaging according to one embodiment.

Thus, the base image and the dynamic image are subjected to threshold processing as shown in FIG. 13 to force S0 and S(t) of blood vessels to be equal to a threshold Sth. That is, pixels corresponding to blood vessel portions in the original image are given to the base image and all images in a time direction at a definite value. Specifically, a given threshold Sth is set, and processing of Equations (5) and (6) is performed on the base image and the dynamic image.

$$S0 < Sth \text{ then } S0 = Sth \quad (5)$$

$$S < Sth \text{ then } S = Sth \quad (6)$$

Furthermore, as shown in FIG. 13, the ratio between the base image and the dynamic image after the threshold processing is obtained to generate a diagnostic image.

In addition, the threshold Sth can be obtained by, for example, signal values of the pixels corresponding to blood vessel portions. That is, for example, among the signal values of the blood vessels in the base image and the dynamic image at the signal values S0, S(t), the maximum value is used as the threshold Sth. In the case of the DSC-MRI, blood vessels can be visualized in the base image alone which ensures the maximum value in the time phase direction before enhancement without any search in the time phase direction, and the threshold Sth can be obtained as the maximum value of the blood vessel portions in the mask. Alternatively, a fixed value set to be greater than a signal value which is generally obtained as a signal value of blood vessels at the signal values S0, St) in the base image and the dynamic image may be used as the threshold Sth.

As a result, even if the signal level of blood vessels is not reduced to the noise level, the blood vessel portions have $S/S0=1$, that is, the same image value at $C=\ln(S0/S)/TE$ that represents the concentration of the contrast agent, so that blood vessels can be completely suppressed. In addition, the threshold Sth can be used together with the threshold for mask creation which is used to remove air. The signal intensity of air is lower than that of blood vessels. Therefore, air portions are inevitably removed by the above-mentioned processing.

Furthermore, an original signal intensity map may not be processed (replacement with S0=Sth, S=Sth) for pixels equal to or less than S0th, Sth, and corresponding parts in a concentration map C may be directly set to zero.

(g) Combination of Different b-Intensities (Dephase (b>0) and b=0/Rephase)

Magnetic resonance signals are acquired (at least one point) by a dephase sequence having b=1 to 10 [sec/mm$^2$] only before enhancement. After enhancement, magnetic resonance signals are acquired by b=0 or rephase sequence. Then, two base images S0D, S0 are reconstructed in accordance with the magnetic resonance signals thus acquired. When magnetic resonance signals are acquired at a plurality of points by a dephase sequence of b=1 to 10 [sec/mm$^2$], these signals are averaged. Further, the following processes are made for a non-AIF method and an AIF method, respectively.

(For Non-AIF Method)

Whether the following relation is satisfied is judged for all the pixels.

$$S0d/S(t) <= 1$$

Then, C(t)=0 is set for the pixels that satisfy this relation, while C(t)=ln [S0/S(t)]/TE is set for the pixels that do not satisfy the relation.

As a result, blood vessels have $S0d=S0<1$ due to a dephase effect, and the concentration C(t) is therefore 0. However, for tissue, $S0d$ and S0 are different, and C(t) which is not 0 is therefore calculated.

(For AIF Method)

In order to obtain an AIF, a normal (standard, rephase) base image may be used instead of the dephase base image to obtain concentration for all pixels by the following normal equation without any conditions.

$$C(t) = \ln [S0/S(t)]/TE$$

AIF and Ca(t) are common to the non-AIF and the AIF, and are extracted from C(t) of all the pixels using a peak value, area and peak reaching time.

Figure 14:
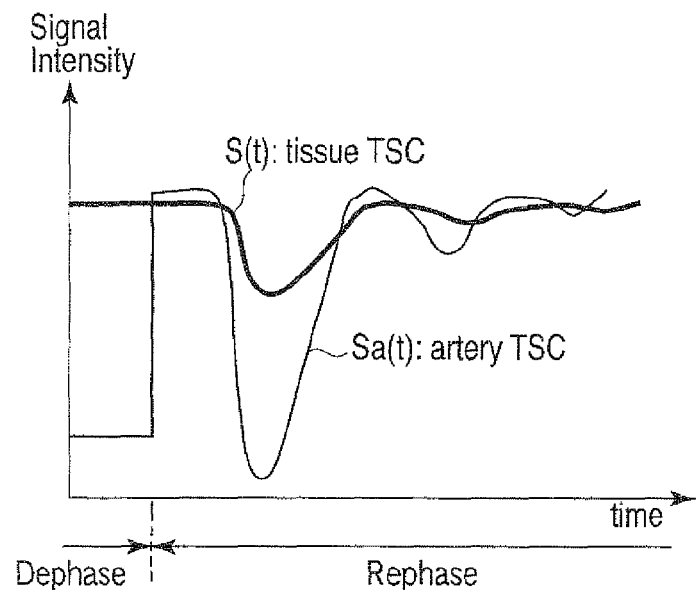
FIG. 14 is a graph showing an original signal intensity-time curve in the case where a base image is obtained by a combination of different b-intensities.
Figure 15:
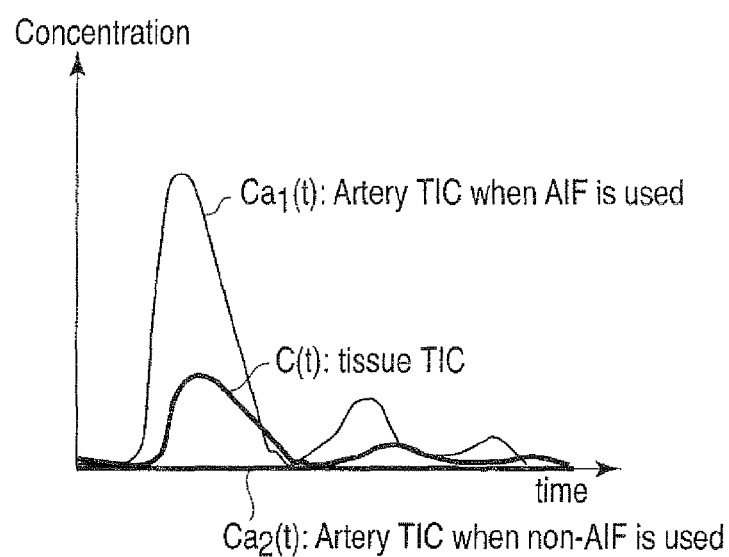
FIG. 15 is a graph showing a concentration-time curve obtained from the original signal intensity-time curve shown in FIG. 14.

FIG. 14 and FIG. 15 are graphs showing an original signal intensity-time curve and a concentration-time curve in this case, respectively.

Thus, according to the present embodiment, it is possible to obtain an image in which tissue including capillary vessels containing blood flowing at a lower velocity is visualized in a more enhanced manner than thick blood vessels such as arteries containing blood flowing at a higher velocity. Consequently, an image useful for the observation of capillary vessels can be obtained.

Furthermore, together with the flow dephase, blood vessel signals which may disturb a perfusion measurement or diagnosis using an angiographic contrast agent can be reduced. Together with the non-AIF method (e.g., a method in which the ratio of C(t) to the reference tissue having the maximum inclination is a CBF index and the ratio of C(t) to the reference tissue having an area under a curve is a CBV index), the CBF, cerebral blood volume (CBV) and mean transit time (MTT) can be semiquantified without any AIF.

Furthermore, together with the flow rephase, it is possible to improve the stability of a generated AIF, improve an SNR in a base line (low concentration) portion in the DCF-MRI, and improve the accuracy and stability in a high concentration portion resulting from a saturation effect in the DSC-MRI.

Still further, blood vessel portions can be identified early before the injection of the contrast agent, so that perfusion analysis processing with the identified blood vessel portions can be accelerated.

Further yet, fMRI dominant to the BOLD signal with suppressed blood vessel artifact is possible.

The following modifications can be made to this embodiment.

(1) The present invention is applicable to the purpose of visualizing fluids other than blood such as a lymph fluid and a cerebrospinal fluid.

Instead of the dephase sequence, any sequence and postprocessing that uses phase information can be combined together and applied. As the postprocessing that uses the phase information, enhancing processing adapted to the phase information using a cosine filter is conceived.

(2) Cosine filter (COS-filter) processing can be applied

Figure 16:
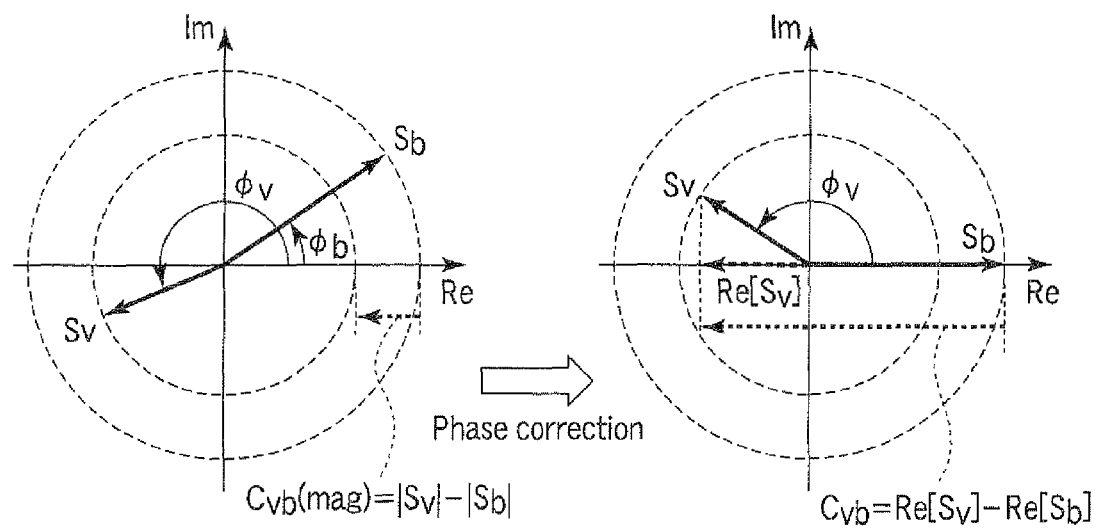
FIG. 16 is a graph showing how a background phase correction is made.

As shown in FIG. 16, a real-part Re[Sv] of a vessel signal Sv after a background phase correction is always negatively smaller than amplitude |Sv|. Therefore, vessel-to-background contrast $C_{vb}$(real) in the real-part is always greater than vessel-to-background contrast $C_{vb}$(mag) in amplitude. However, $C_{vb}$(mag)=|Sv|−|Sb|.

Figure 17:
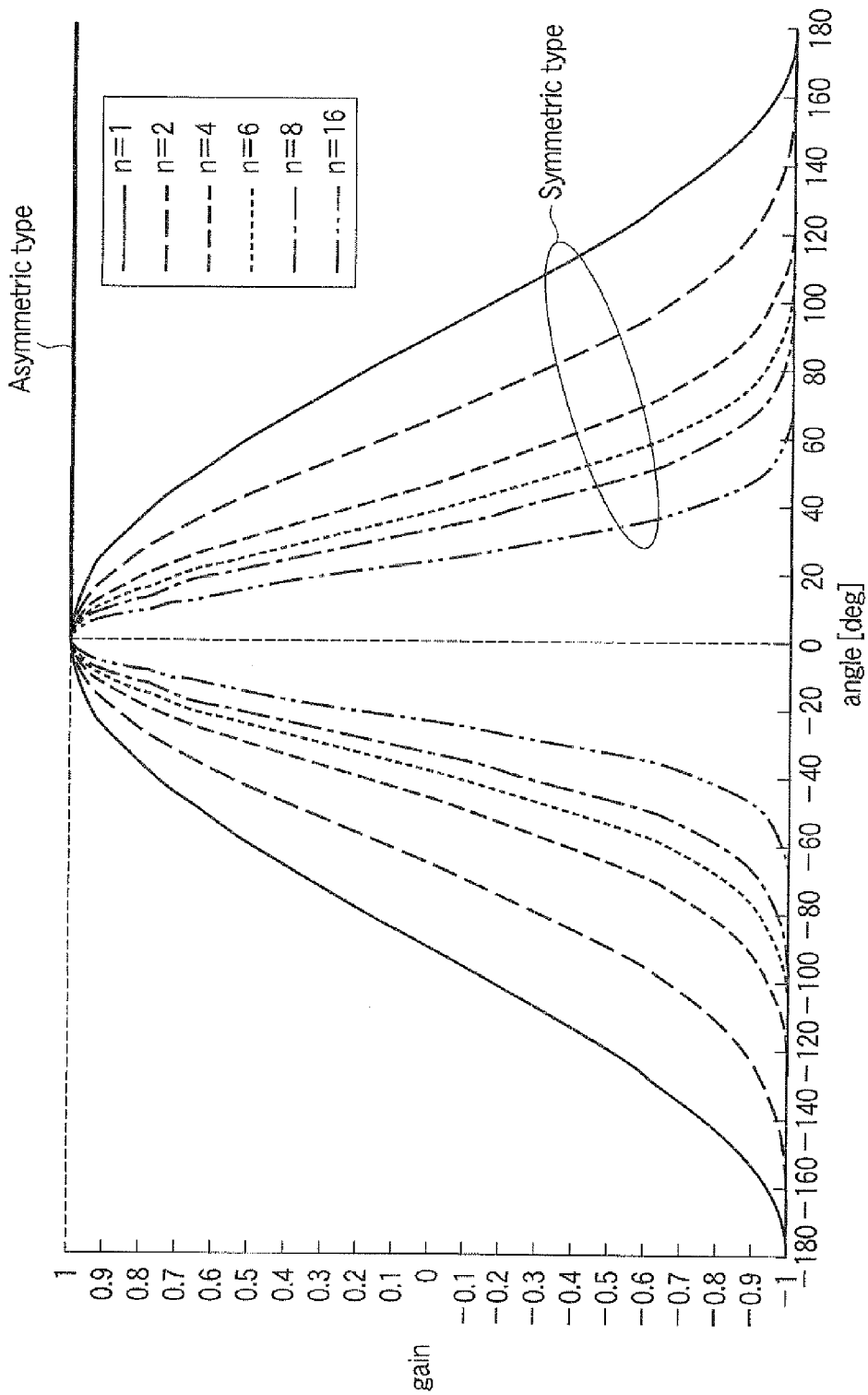
FIG. 17 is a graph showing the characteristics of cosine filters.

FIG. 17 is a graph showing the characteristics of the cosine filter.

The cosine filter for black-blood is a phase filter to enhance blood vessels in a BB image, and is based on a cosine function for phases.

A cosine filter $H_B$ is represented by the following equation.

$$H_B = 2 \times (M^n - 0.5)$$

Here, there are an asymmetric type cosine filter and a symmetric type cosine filter. M for the asymmetric type cosine filter is determined as in the following equation if a condition $Im[S_{cor}]<0$ or a condition $\phi_{cor}<0$ is satisfied, or M is set at 0 if neither of the conditions is satisfied.

$$M = \{\cos(\phi_{cor}) + 1\}/2$$

M for the symmetric type cosine filter is determined as in the following equation without any conditions.

$$M = \{\cos(\phi_{cor}) + 1\}/2$$

Furthermore, n is an enhancement factor. The enhancement factor n is a value equal to or more than 0, and enhancement is stronger when the enhancement factor n is higher.

The cosine filter processing is signal enhancement processing using real-part information. To be more specific, the cosine filter processing is processing wherein a blood vessel signal is enhanced against a background signal by varying a signal value in accordance with the above characteristics on the basis of the real-part information. When the cosine filter processing is executed for a BB image, the signal value of the blood vessel signal negatively increases relative to the background signal.

Performing the cosine filter processing of n=1 after a phase correction is equivalent to taking the real-part. Performing the cosine filter processing of n>1 is equivalent to enhancing the phase in a 180° direction and taking the real-part. In addition, an actual phase is often underestimated in a background phase correction using a homodyne filter which is carried out before the cosine filter, and $C_{vb}$(real) is negatively maximized when a blood vessel phase $\phi_v$ after the correction is 180°. Thus, if the cosine filter processing of n>1 is performed, $\phi_V$ can be equivalently brought closer to 180°.

Figure 18:
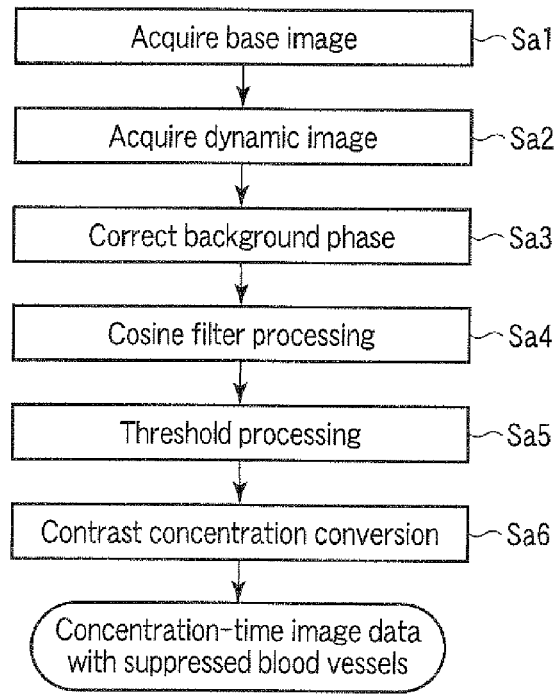
FIG. 18 is a flowchart showing one example of an imaging procedure for performing cosine filter processing.
Figure 19:
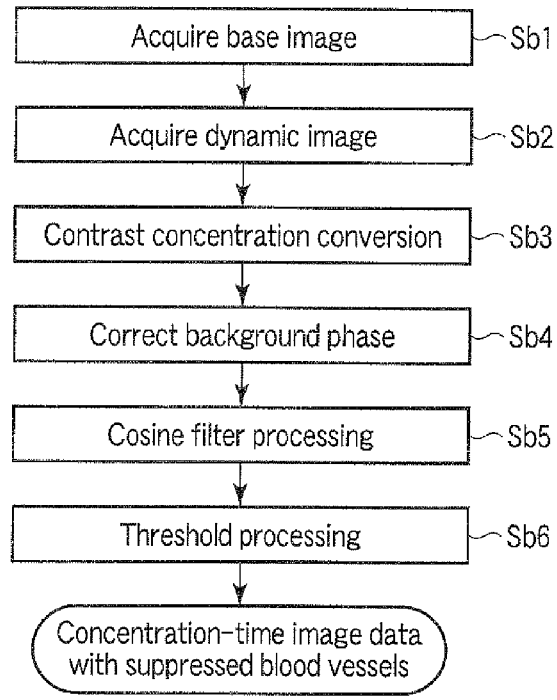
FIG. 19 is a flowchart showing one example of an imaging procedure for performing cosine filter processing.

FIG. 18 and FIG. 19 are flowcharts showing examples of imaging procedures for performing the cosine filter processing.

The imaging procedure shown in FIG. 18 illustrates an example in which blood vessels are masked by the cosine filter before concentration conversion. In this case, the procedure is carried out in the following order: acquisition of the base image (step Sa1), acquisition of the dynamic image (step Sa2), correction of background phase (step Sa3), cosine filter processing (step Sa4), threshold processing (step Say) and contrast concentration conversion (step Sa6).

The imaging procedure shown in FIG. 19 illustrates an example in which blood vessels are masked by the cosine filter after concentration conversion. In this case, the procedure is carried out in the following order: acquisition of the base image (step Sb1), acquisition of the dynamic image (step Sb2), contrast concentration conversion (step Sb3), correction of background phase (step Sb4), cosine filter processing (step Sb5) and threshold processing (step Sb5).

Next, the effect of the cosine filter processing in the DSC-MRI that uses a negative contrast agent is described. The relation between a real-part signal and amplitude is described to help clear understanding in the explanation associated with a complex plane.

FIG. 20 and FIG. 21 are graphs showing one example of blood vessel signals after the background phase correction and the cosine filter processing and before and after enhancement. The blood vessel signals before and after enhancement have the same polarity in the case shown in FIG. 20, and the blood vessel signals before and after enhancement have reverse polarities in the case shown in FIG. 21.

As shown in FIG. 20 and FIG. 21, if complex signals before and after enhancement are S0 and S, respectively, a phase shift attributed to the magnetic susceptibility effect of the contrast agent is further added under the same condition regardless of whether there is an MPG. Thus, before the cosine filter processing, that is, in amplitude, Re[S0]<|S0|, Re[S]<|S| even if |S0|>|S|.

FIG. 22 is a graph showing the effect of the cosine filter processing in the form of blood vessel and background spatial profiles.

In FIG. 22, regarding the blood vessel portions, signal values based on amplitude information are indicated by broken lines, and signal values after the cosine filter processing are indicated by full lines. Dashed lines indicate the signal ratio between the base image after the cosine filter processing and the contrast image without the cosine filter processing. Further, the left side of FIG. 22 shows a profile without the threshold processing, and the right side shows a profile after the threshold processing. In addition, a threshold substantially equal to the noise level is used for the threshold processing.

As apparent from FIG. 22, the signal value of blood vessels in the base image is decreased by the cosine filter processing. When the phase of the signal regarding the blood vessels is beyond 90 degrees, the signal value of the blood vessels in the base image after the cosine filter processing is negative. The signal value difference between blood vessels and tissue can be thus increased by the application of the cosine filter processing, so that blood vessels can be easily distinguished from tissue by the threshold processing. Moreover, the noise level or zero can be used as a threshold in the threshold processing.

$\Delta R2^*$ after the concentration conversion is ln [Re[S0]/|S|] <ln [|S0|/|S|] even in the limited case where ln has the same sign and is >0 and the signal value can therefore be computed. That is, the signal value is lower and the blood vessel suppression effect is higher when the cosine filter processing is applied only before enhancement than when the cosine filter processing is applied neither before nor after enhancement. In addition, the signal value cannot be computed when ln is <0.

In that case, there is a high probability of blood vessels because the difference of phases before and after enhancement is great. Thus, regarding as blood vessels, the concentration may be set at, for example 0. The threshold processing when the cosine filter processing is used can be omitted if the MPG is sufficiently great and can be reduced to about the noise level as in the case of amplitude. However, in order to take advantage of the cosine filter processing capable of reduction without a great MPG provided, it is desirable to enhance a phase to near 180° to produce a negative signal and perform threshold processing substantially at the noise level.

Furthermore, the phase shift of tissue may vary depending on the strength of the cosine filter and the concentration of the contrast agent. Thus, in order for the cosine filter processing to have no influence on tissue, an amplitude image is preferably used as it is except for the range which has been extracted as blood vessels by the threshold processing. To this end, an image mask to be put over the amplitude image is set at 1, and the blood vessels alone are set at 0. Such a blood suppression mask is easily created because the gain of the cosine filter HE can set, to nearly 1, the background tissue portions where the phase shift is negligible. The cosine filter is significantly nonlinear as such, and can keep the gain at nearly 1 against some variations in the case of a phase near zero. However, if there are further needs, the shape of a BB cosine filter may be changed step by step using the threshold of the phase. For example, the filter is set as follows:

$$Hb=1:|\phi|<\phi_{th1}, =0.5(1-M^n):\phi_{th1}<|\phi|<\phi_{th2}, =0:\phi_{th2}<|\phi|$$

wherein $\phi_{th1}$ is a threshold to separate background tissue from blood vessels, and $\phi_{th2}$ is a threshold to separate the part which is equal to or more than the upper limit of the blood vessels and which is a static tissue having a high magnetic susceptibility. Moreover, steps in the phase direction may be smoothly linked together.

When cosine filters are combined together, the MPG may be applied or may not be applied in at least the acquisition of the base image. The advantage of not applying the MPG is that a normal pulse sequence can be used. However, in this case, there is no phase shift in blood vessels in the base image because no contrast agent is contained, so that the effect of the cosine filter processing cannot be expected. Therefore, in this case, the cosine filter processing is applied to the image after enhancement to create a mask in which blood vessels are extracted (background tissue at 1, blood vessels at 0), and this mask is used to suppress the blood vessel portions. In the cosine filter processing, the cosine filter can remain at 1, that is, at the amplitude even after enhancement if the phase shift in the background tissue is sufficiently small. To this end, if a peak height map is used which is a map of the maximum value of the contrast agent concentration in the time direction that has its time range limited to an artery phase, the influence on the tissue can be reduced because there is a high probability that no shift has been made to tissue only in artery portions.

Since the end is to suppress the blood vessels in a concentration image, the step of applying the cosine filter processing, that is, the step of applying the spatial mask to be put over the amplitude image may be implemented on the original image or on the image after concentration conversion as long as attention is paid to exceptions such as division by a negative value or zero described in the embodiment (in the case of the procedure shown in FIG. 19). The advantage in this case is that processing can be carried out by a common method regardless of whether a contrast agent is negative or positive.

Furthermore, the cosine filter processing is applicable not only to the negative enhancement but also to a positive contrast agent or the fMRI.

However, the positive is different from the negative in that the cosine filter processing is applied not to the base image but to at least data after enhancement when the cosine filter processing is applied to the original image. This holds true with the suppression of blood vessels by the application of the MPG.

The effects of the cosine filter processing described above can be summarized as follows:
   Suppression effect can be improved by the improvement of the vessel-to-background contrast.
   Dephasing by the MPG can be omitted.
   An image mask to exclude blood vessels is created solely from the base image, and this image mask is desirably applied to the original image or the concentration image even after enhancement.

In the case described above, the cosine filter processing is applied to make a contrast between blood vessels and tissue in the BB image or to enhance the contrast. However, the cosine filter processing can also be applied to make a contrast between blood vessels and tissue in the WB image or to enhance the contrast. The cosine filter used in this case has such characteristics that the gain is smaller when the phase is closer to 0, as opposed to the characteristics shown in FIG. 17.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus comprising:
   an acquisition unit which acquires, by a first sequence, a magnetic resonance signal generated in an imaging region before administration of a contrast agent and which also acquires, by a second sequence, magnetic resonance signal generated in the imaging region after the administration of the contrast agent, the first sequence dephasing a magnetization after radio frequency excitation to make a greater signal reduction in a first magnetic resonance signal component regarding a fluid flowing within a first flow velocity range than in a second magnetic resonance signal component regarding the fluid flowing within a second flow velocity range less than the first flow velocity range, the second sequence bringing the magnetic resonance signal generated in the imaging region after the administration of the contrast agent to a level corresponding to the concentration of the contrast agent;
   a reconstruction unit which reconstructs a first image and a second image on the basis of the magnetic resonance signals respectively acquired by the first and second sequences, the first image and the second image showing spatial distributions of the fluid in the imaging region to reflect the intensities of the magnetic resonance signals; and
   a generation unit which generates a third image on the basis of the first image and the second image, the third image showing the degree of a change of the fluid after the administration of the contrast agent from a state before the administration of the contrast agent.

2. The magnetic resonance imaging apparatus according to claim 1, wherein the reconstruction unit reconstructs the first image and the second image to show spatial distributions of signal values corresponding to the magnetic resonance signals generated in the imaging region, and the generation unit uses a threshold to perform threshold processing of the signal values included in the first image and the second image, and generates the third image on the basis of the first image and the second image after the threshold processing, the threshold being set as an intermediate value between a signal value corresponding to the level of the first magnetic resonance signal component before the administration of the contrast agent and a signal value corresponding to the level of the second magnetic resonance signal component.

3. The magnetic resonance imaging apparatus according to claim 1, wherein the acquisition unit acquires, not only by the first sequence but also by a third sequence, the magnetic resonance signal generated in the imaging region before the administration of the contrast agent, the third sequence being smaller than the first sequence in the amount of signal reduction of the first magnetic resonance signal component compared with the second magnetic resonance signal component,
the reconstruction unit reconstructs a fourth image on the basis of the magnetic resonance signal acquired by the third sequence, the fourth image showing a spatial distribution of the fluid in the imaging region to reflect the intensity of the magnetic resonance signal, and
the generation unit generates the third image on the basis of the first image, the second image and the fourth image.

4. The magnetic resonance imaging apparatus according to claim 1, wherein the acquisition unit causes the magnetization after the radio frequency excitation to be dephased by a motion probing gradient MPG) pulse, and uses, as a b-factor, a value which makes a greater signal reduction in the fluid flowing within the first flow velocity range than in the fluid flowing within the second flow velocity range.

5. The magnetic resonance imaging apparatus according to claim 1, wherein the acquisition unit reduces the signal intensity of a magnetic resonance signal component regarding the fluid flowing at a flow velocity within a first flow velocity range to a level substantially equal to the signal intensity of a magnetic resonance signal component regarding a substance other than the fluid.

6. The magnetic resonance imaging apparatus according to claim 1, wherein the reconstruction unit reconstructs the first image or the second image to show, in a more enhanced state, the fluid which has generated a greater magnetic resonance signal.

7. The magnetic resonance imaging apparatus according to claim 1, wherein the first sequence is a sequence based on a black blood method which reduced a blood vessel signal by including a gradient magnetic field dephase pulse to visualize blood vessels in black.

8. A magnetic resonance imaging apparatus comprising:
an acquisition unit which acquires, by a dephase sequence, a magnetic resonance signal generated in an imaging region, the dephase sequence dephasing a magnetization after radio frequency excitation to make a greater signal reduction in a fluid flowing within a first flow velocity range than in the fluid flowing within a second flow velocity range less than the first flow velocity range; and
a reconstruction unit which reconstructs an image on the basis of the magnetic resonance signal acquired by the acquisition unit, the image showing a spatial distribution of the fluid in the imaging region to reflect the intensity of the magnetic resonance signal.

9. The magnetic resonance imaging apparatus according to claim 8, wherein the acquisition unit causes the magnetization after the radio frequency excitation to be dephased by a motion probing gradient (MPG) pulse, and uses, as a b-factor, a value which makes a greater signal reduction in the fluid flowing within the first flow velocity range than in the fluid flowing within the second flow velocity range.

10. The magnetic resonance imaging apparatus according to claim 8, wherein the acquisition unit reduces the signal intensity of a magnetic resonance signal component regarding the fluid flowing at a flow velocity within a first flow velocity range to a level substantially equal to the signal intensity of a magnetic resonance signal component regarding a substance other than the fluid.

11. The magnetic resonance imaging apparatus according to claim 8, wherein the reconstruction unit reconstructs the first image, the second image or the image to show, in a more enhanced state, the fluid which has generated a greater magnetic resonance signal.

12. A magnetic resonance imaging apparatus comprising:
an acquisition unit which performs imaging of a subject before administration of a negative contrast agent by a black blood method and performs dynamic imaging of the subject after the administration of the negative contrast agent by a predetermined imaging method, the black blood method reducing a blood vessel signal including a gradient magnetic field dephase pulse to visualize blood vessels in black;
a reconstruction unit which reconstructs a base image on the basis of a magnetic resonance signal obtained by the imaging of the subject before the administration of the negative contrast agent and also reconstructs a contrast image of multiple time phases on the basis of a magnetic resonance signal obtained by the dynamic imaging of the subject after the administration of the negative contrast agent; and
a generation unit which generates a diagnostic image on the basis of the base image and the contrast image.

13. A magnetic resonance imaging apparatus comprising:
an acquisition unit which acquires a magnetic resonance signal generated in an imaging region under a first condition and a second condition, the first condition causing the signal level of a first magnetic resonance signal component regarding a fluid flowing within a first flow velocity range to be different in a prescribed direction from the signal level of a second magnetic resonance signal component regarding the fluid flowing within a second flow velocity range less than the first flow velocity range, the second condition causing the signal level of the first magnetic resonance signal component to be different in the prescribed direction from the signal level of the second magnetic resonance signal component, the signal levels of the first and second magnetic resonance signal components being different in the prescribed direction from the signal levels thereof in the first condition, the amount of change of the first magnetic resonance signal component being greater than that of the second magnetic resonance signal component in the second condition;
a reconstruction unit which reconstructs a first image and a second image on the basis of the magnetic resonance signals respectively acquired under the first and second conditions, the first image and the second image showing spatial distributions of the fluid in the imaging region to reflect the intensities of the magnetic resonance signals; and
a generation unit which generates a third image on the basis of the first image and the second image, the third image showing the degrees of signal level changes in the first condition and the second condition.

14. The magnetic resonance imaging apparatus according to claim 13, wherein the first flow velocity range is set to include the flow velocities of blood in arteries and veins, and the second flow velocity range is set to include the flow velocity of blood in capillary vessels.

15. The magnetic resonance imaging apparatus according to claim 13, wherein the acquisition unit sets the first and second conditions so that the signal level of the second magnetic resonance signal component is lower than the signal level of the first magnetic resonance signal component.

16. The magnetic resonance imaging apparatus according to claim 13, wherein the acquisition unit sets the first and second conditions so that the signal level of the second magnetic resonance signal component is higher than the signal level of the first magnetic resonance signal component.

17. The magnetic resonance imaging apparatus according to claim 13, wherein the acquisition unit executes cosine filter processing that increases the difference between the signal level of the first magnetic resonance signal component and the signal level of the second magnetic resonance signal component based on real-part information.

* * * * *